United States Patent
Yokoi (10) Patent No.: US 12,018,241 B2
(45) Date of Patent: Jun. 25, 2024

(54) MICROBIOTA TRAPPING DEVICE, MICROBIOTA TRAPPING APPARATUS, AND MICROBIOTA TRAPPING METHOD

(71) Applicant: Hitachi High-Tech Corporation, Tokyo (JP)

(72) Inventor: Takahide Yokoi, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 741 days.

(21) Appl. No.: 17/014,602

(22) Filed: Sep. 8, 2020

(65) Prior Publication Data

US 2021/0108168 A1    Apr. 15, 2021

(30) Foreign Application Priority Data

Oct. 11, 2019    (JP) .................. 2019-187245

(51) Int. Cl.
| | | |
|---|---|---|
| *C12M 3/00* | (2006.01) | |
| *B01D 63/08* | (2006.01) | |
| *B01L 3/00* | (2006.01) | |
| *C12M 1/12* | (2006.01) | |
| *C12M 1/34* | (2006.01) | |

(52) U.S. Cl.
CPC ........... *C12M 25/02* (2013.01); *B01D 63/087* (2013.01); *C12M 23/48* (2013.01); *C12M 41/40* (2013.01); *B01D 2313/16* (2013.01); *B01D 2313/24* (2013.01); *B01D 2313/50* (2013.01)

(58) Field of Classification Search
CPC ........... B01D 2313/16; B01D 2313/24; B01D 2313/50; B01D 61/18; B01D 63/087; B01L 2200/0668; B01L 2300/047; B01L 2300/0681; B01L 2400/0487; B01L 3/50825; C12M 23/48; C12M 25/02; C12M 41/40; C12N 15/1017; G01N 2001/4088

See application file for complete search history.

(56) References Cited

U.S. PATENT DOCUMENTS

| | | | |
|---|---|---|---|
| 8,679,828 B2 | 3/2014 | Okanojo et al. | |
| 2010/0012589 A1* | 1/2010 | Ribault | G01N 1/4077 435/287.1 |
| 2012/0301907 A1 | 11/2012 | Sellappan et al. | |

(Continued)

FOREIGN PATENT DOCUMENTS

| | | |
|---|---|---|
| JP | H02255074 A | 10/1990 |
| JP | 2010025931 A | 2/2010 |

(Continued)

OTHER PUBLICATIONS

Japanese Patent Office, Notice of Reasons for Refusal, Application No. JP2019-187245, dated Apr. 25, 2023, in 8 pages.

(Continued)

*Primary Examiner* — Nathan A Bowers
(74) *Attorney, Agent, or Firm* — PROCOPIO, CORY, HARGREAVES & SAVITCH LLP (57) ABSTRACT

Provided is a technique for easily trapping microbiota in a sample. A microbiota trapping device of the present disclosure includes a first solution tank having a first filter adapted to trap residue in a sample, and a second solution tank having a second filter adapted to trap bacteria in the sample. The second solution tank has a vent above the second filter.

5 Claims, 7 Drawing Sheets

(56) References Cited

U.S. PATENT DOCUMENTS

2015/0140583 A1* 5/2015 Hearn ............... C12Q 1/66
                                                422/534
2016/0216177 A1* 7/2016 Rivat ............... B01L 3/5635

FOREIGN PATENT DOCUMENTS

| WO | 96036428 A1 | 11/1996 |
| WO | 2017143452 A1 | 8/2017 |
| WO | 2018075250 A1 | 4/2018 |

OTHER PUBLICATIONS

Costea, P. et al. "Towards standards for human fecal sample processing in metagenomic studies" Nature Biotechnology, Oct. 2, 2017, (11 pages).
Kim, S. et al. "Robustness of Gut Microbiota of Healthy Adults in Response to Probiotic Intervention Revealed by High-Throughput Pyrosequencing" DNA Research 20, Apr. 9, 2013, pp. 241-253; vol. 20; No. 3; (13 pages).
Preliminary Search Report dated Oct. 28, 2021 from counterpart FR Patent Application No. 2009036, 8 pages.

\* cited by examiner

MICROBIOTA TRAPPING DEVICE, MICROBIOTA TRAPPING APPARATUS, AND MICROBIOTA TRAPPING METHOD

CROSS REFERENCE TO RELATED APPLICATIONS

The present application claims priority from Japanese patent application JP 2019-187245 filed on Oct. 11, 2019, the entire content of which is hereby incorporated by reference into this application.

BACKGROUND

Technical Field

The present disclosure relates to a microbiota trapping device, a microbiota trapping apparatus, and a microbiota trapping method.

Background Art

In recent years, indigenous microbiota, which is a bacterial group residing in the human body, has been attracting attention as a new biomarker or a target for therapy. The conventional research of microbiota inevitably involves the growth of bacteria through cultivation. Thus, it has been difficult to detect nonculturable bacteria and thus has been impossible to comprehensively analyze microbiota. Meanwhile, with a technique of analyzing microbiota genes using the next-generation sequencer developed in recent years, it has become possible to comprehensively analyze microbiota-derived genes through amplification without cultivation. Thus, it has become possible to comprehensively identify microbiota and make a comparison among a diversity of bacterial species in the microbiota.

However, as disclosed in Non Patent Literature 1 (Costea et al., Towards standards for human fecal sample processing in metagenomic studies nature biotechnology, 2017, 1-9), a DNA extraction technique from microbiota is still immature. For example, variation in the measurement results due to different reagents and/or kits used, and variation in operation due to different engineers involved in the operation even with the same kit are the major barriers to the development of the research of microbiota. It is supposed that accumulating pieces of microbiota data that can be mutually compared with one another will greatly contribute to the promotion of the research of intestinal microbiota, and it is desired to automate a DNA extraction technique that is a preprocessing step of a microbiota gene analysis technique.

A technique of extracting DNA from microbiota is broadly divided into a direct extraction method and an indirect extraction method. The direct extraction method is a technique of physically and directly disrupting a sample containing microbiota using bead-beating, for example, and then extracting DNA from the sample solution and refining it. The direct extraction method is advantageous in its ease of operation. However, the method is problematic in that DNA derived from components (e.g., human cells or food residue) other than bacteria contained in the sample would be mixed or desired DNA would be fragmented into a size of several kb or less due to the physical process performed.

The indirect extraction method is a technique of once separating bacterial cells from a sample and then extracting DNA from the separated bacterial cells. Since DNA is extracted from the separated microbiota through a gentle process in the indirect extraction method, it can recover large-fragment DNA having a size of over 20 kb and having no other organisms mixed therein (Non Patent Literature 2: Kim et al., Robustness of Gut Microbiota of Healthy Adults in Response to Probiotic Intervention Revealed by High-Throughput Pyrosequencing, DNA RESEARCH 2013, 20, 241-253). However, the indirect extraction method is problematic in that it involves a burdensome operation compared with the direct extraction method.

The current mainstream intestinal microbiota research is conducted by comparing the components of intestinal microbiota. In the future, it is supposed that the research will further advance to the analysis of the function of intestinal microbiota. The DNA fragment length that is required for the identification of a bacterial species is several hundred bp. Therefore, although many institutions use the direct extraction method at present, the indirect extraction method is more suitable for analyzing the function of microbiota as it can prepare large-fragment DNA with which analysis of a gene structure is possible.

SUMMARY

In Non Patent Literature 2, centrifugation is performed to trap microbiota from a sample after residue has been removed from the sample through a filter. However, such a step is complex, and in particular, performing a centrifugation process is burdensome for the operator.

Accordingly, the present disclosure provides a technique for easily trapping microbiota from a sample.

In view of the foregoing, a microbiota trapping device of the present disclosure includes a first solution tank having a first filter adapted to trap residue in a sample, and a second solution tank having a second filter adapted to trap bacteria in the sample, and the second solution tank has a vent above the second filter.

Further features related to the present disclosure will become apparent from the description of this specification and the accompanying drawings. In addition, embodiments of the present disclosure can be implemented by elements, a combination of a variety of elements, the following detailed description, and the appended claims.

The description of this specification contains only typical illustrative examples. Therefore, claims or examples of the application of the present disclosure should not be limited in any sense.

According to the microbiota trapping device of the present disclosure, microbiota can be easily trapped from a sample.

Problems, configurations, and advantageous effects other than those described above will become apparent from the following description of embodiments.

DETAILED DESCRIPTION

Throughout the drawings for illustrating the following embodiments, elements having the same function are denoted by the same reference numeral. Thus, the repeated description thereof will be omitted as much as possible. In addition, the present disclosure should not be construed as being limited to the description of the following embodiments. One of ordinary skill in the art will easily understand that the specific configuration of the present disclosure can be changed without departing from the spirit and scope thereof.

There may be cases where the position, size, shape, range, and the like of each structure illustrated in the drawings do not represent the actual position, size, shape, range, and the like of the structure to help easily understand the invention. Therefore, the present disclosure is not necessarily limited to the position, size, shape, range, and the like of each structure disclosed in the drawings.

In addition, the publications cited in this specification partly constitute the description of this specification.

Each constituent element represented in a singular form in this specification includes a plural form unless explicitly stated to the contrary in context.

In the present disclosure, "large-fragment DNA" refers to DNA with a size greater than or equal to 20 kb that is the upper limit allowing for observation through separation in typical agarose gel electrophoresis.

First Embodiment

<Configuration of Microbiota Trapping Apparatus>

Figure 1:
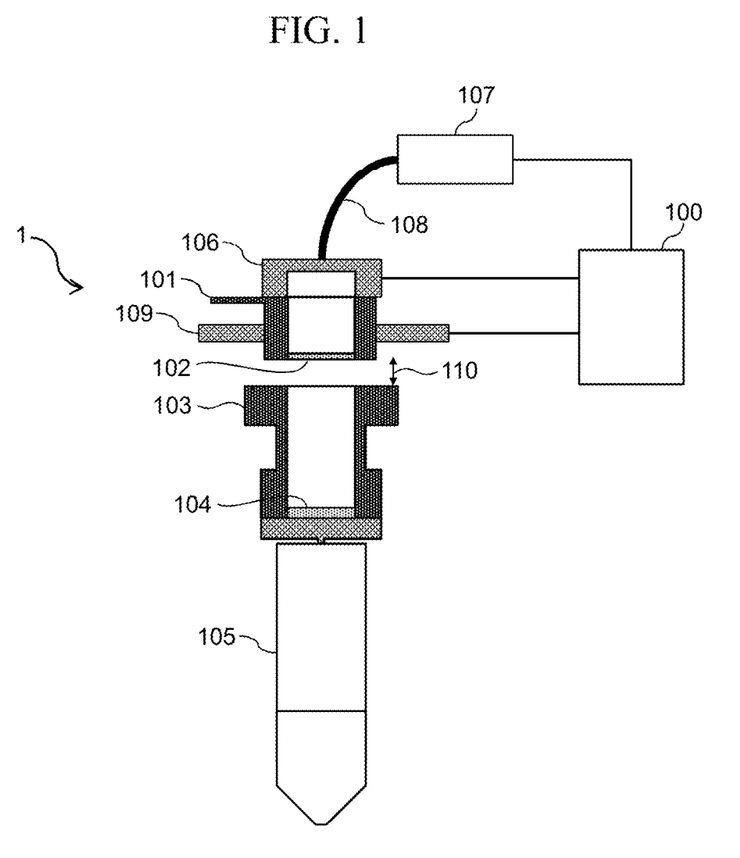
FIG. 1 is a schematic view of a microbiota trapping apparatus according to a first embodiment.

FIG. 1 is a schematic view of a microbiota trapping apparatus according to a first embodiment. As illustrated in FIG. 1, the microbiota trapping apparatus includes a microbiota trapping device 1, a control device 100, a pressure pump 107, and a tube 108. FIG. 1 illustrates a cross-section of the microbiota trapping device 1. The microbiota trapping device 1 includes a first solution tank 101, a second solution tank 103, a waste liquid container 105, a pressure container 106, and a support 109.

At least part of the bottom face of the first solution tank 101 is formed of a residue removing filter 102 (i.e., a first filter), and a sample solution (i.e., a sample) is introduced into the first solution tank 101 through an opening thereof. It is also possible to use a filter holder having openings at its top and bottom as the first solution tank 101 and dispose the residue removing filter 102 at the bottom of the filter holder.

The residue removing filter 102 can trap residue in a sample. The pore size of the residue removing filter 102 can be set to greater than or equal to 70 μm, for example. As the material of the residue removing filter 102, either a hydrophobic material or a hydrophilic material can be used. Examples of the hydrophobic material include polyamide, fluorine resin such as polytetrafluoroethylene, polyolefin such as polypropylene, polycarbonate, and glass. Examples of the hydrophilic material include polyether sulfone resin, cellulose acetate, and nitrocellulose.

The second solution tank 103 is disposed below the first solution tank 101 and receives a filtrate that has passed through the residue removing filter 102. The second solution tank 103 has disposed at its bottom a bacteria trapping filter 104 (i.e., a second filter). The bacteria trapping filter 104 is a membrane filter formed of the aforementioned hydrophilic material, for example. The bacteria trapping filter 104 has a pore size capable of trapping bacteria (typically, with a diameter of about 1 to 10 μm), which can thus be set to less than or equal to 1 μm, for example, or less than or equal to 0.45 μm according to circumstances. In this manner, as the pore size of the bacteria trapping filter 104 located below is smaller than that of the residue removing filter 102, bacteria can be trapped from the filtrate that has been obtained by removing residue from the sample solution.

The inside diameter of the first solution tank 101 and that of the second solution tank 103 can be set approximately equal, for example. Alternatively, setting the inside diameter of the second solution tank 103 greater than or equal to that of the first solution tank 101 will allow a sample solution filtered through the residue removing filter 102 to be introduced into the second solution tank 103 more reliably.

The waste liquid container 105 is disposed below the second solution tank 103 and receives a filtrate that has passed through the bacteria trapping filter 104. The waste liquid container 105 may have any structure and be disposed at any position that can prevent scattering of the filtrate from the bacteria trapping filter 104, and may also be coupled to the second solution tank 103 via a liquid supply tube, for example.

The support 109 supports the first solution tank 101 such that a gap 110 is formed between the first solution tank 101 and the second solution tank 103. The size of the gap 110 is not limited to a particular value, but is preferably as small as possible from the perspective of preventing contamination from the outside. In this manner, providing the gap 110 above the second solution tank 103 allows the opening of the second solution tank 103 to serve as a vent. Thus, even when the first solution tank 101 is pressurized, a pressure inside the second solution tank 103 can be maintained at an atmospheric pressure. In this manner, pressurization of the first solution tank 101 and pressurization of the second solution tank 103 can be performed independently.

The support 109 may be configured to be movable in three axial directions by means of a support actuator (not illustrated), for example. Accordingly, the positional relationship between the first solution tank 101 and the second solution tank 103 can be changed. Alternatively, the positional relationship between the first solution tank 101 and the second solution tank 103 may be changed by a user. Although FIG. 1 illustrates an example in which the support 109 supports the first solution tank 101 by gripping it, the present disclosure is not limited thereto and any structure may be provided that allows the gap 110 to be formed between the first solution tank 101 and the second solution tank 103. For example, bars for supporting the bottom face of the first solution tank 101 may be provided at the upper edge of the second solution tank 103, and such bars may be used as the support 109.

Although the pressure container 106 (i.e., a pressure applicator) in FIG. 1 is attached to the first solution tank 101 so as to hermetically seal it by covering its opening, the pressure container 106 is attachable to and detachable from each of the first solution tank 101 and the second solution tank 103. The pressure container 106 may be a lid that covers the opening of the first solution tank 101 or the second solution tank 103. The pressure container 106 has a port (not illustrated) for attachment to the tube 108, and is coupled to the pressure pump 107 (i.e., a pressure applicator) via the tube 108. A pressure generated by the pressure pump 107 is supplied to the pressure container 106 via the tube 108. It is also possible to couple two or more pressure containers 106 to the pressure pump 107, and use the respective pressure containers 106 for the first solution tank 101 and the second solution tank 103.

In this manner, a pressure generated by the pressure pump 107 can be applied to the solution tank 101 or 103 having the pressure container 106 attached thereto. This allows the pressure to act on the filter (i.e., the residue removing filter 102 or the bacteria trapping filter 104) provided on the solution tank, and thus allows a sample solution to be filtered through the filter.

Though not illustrated, the microbiota trapping apparatus may also include a sample container actuator for moving a sample container containing a sample solution. In such a case, driving the sample container actuator can introduce a sample solution into the first solution tank 101. In addition, the microbiota trapping apparatus may also include a pressure container actuator for controlling the movement of the pressure container 106 as well as the attachment/detachment of the pressure container 106 to/from the first solution tank 101 or the second solution tank 103.

Further, the microbiota trapping apparatus may also include a first dispensing nozzle for dispensing a cleaning solution into the first solution tank 101 or the second solution tank 103, a second dispensing nozzle (i.e., a dispenser or a recoverer) for dispensing a recovery solution for recovering bacteria into the second solution tank 103, and a dispensing nozzle actuator for driving the first dispensing nozzle or the second dispensing nozzle. As the cleaning solution and the recovery solution, a buffer solution, such as a PBS solution or a TE solution, can be used, for example. With the second dispensing nozzle, it is also possible to obtain a microbiota suspension by pipetting a mixed solution of bacteria and a recovery solution up and down. The microbiota suspension may be recovered using the second dispensing nozzle or another dispensing nozzle (i.e., a recoverer).

The control device 100 (i.e., a controller) controls the generation of a pressure by the pressure pump 107, drive of each actuator, and drive of each dispensing nozzle. The microbiota trapping apparatus of the present embodiment may include more than one microbiota trapping device 1, and in such a case, the operation of the more than one microbiota trapping device 1 may be controlled with a single control device 100.

<Microbiota Trapping Method>

Figure 2:
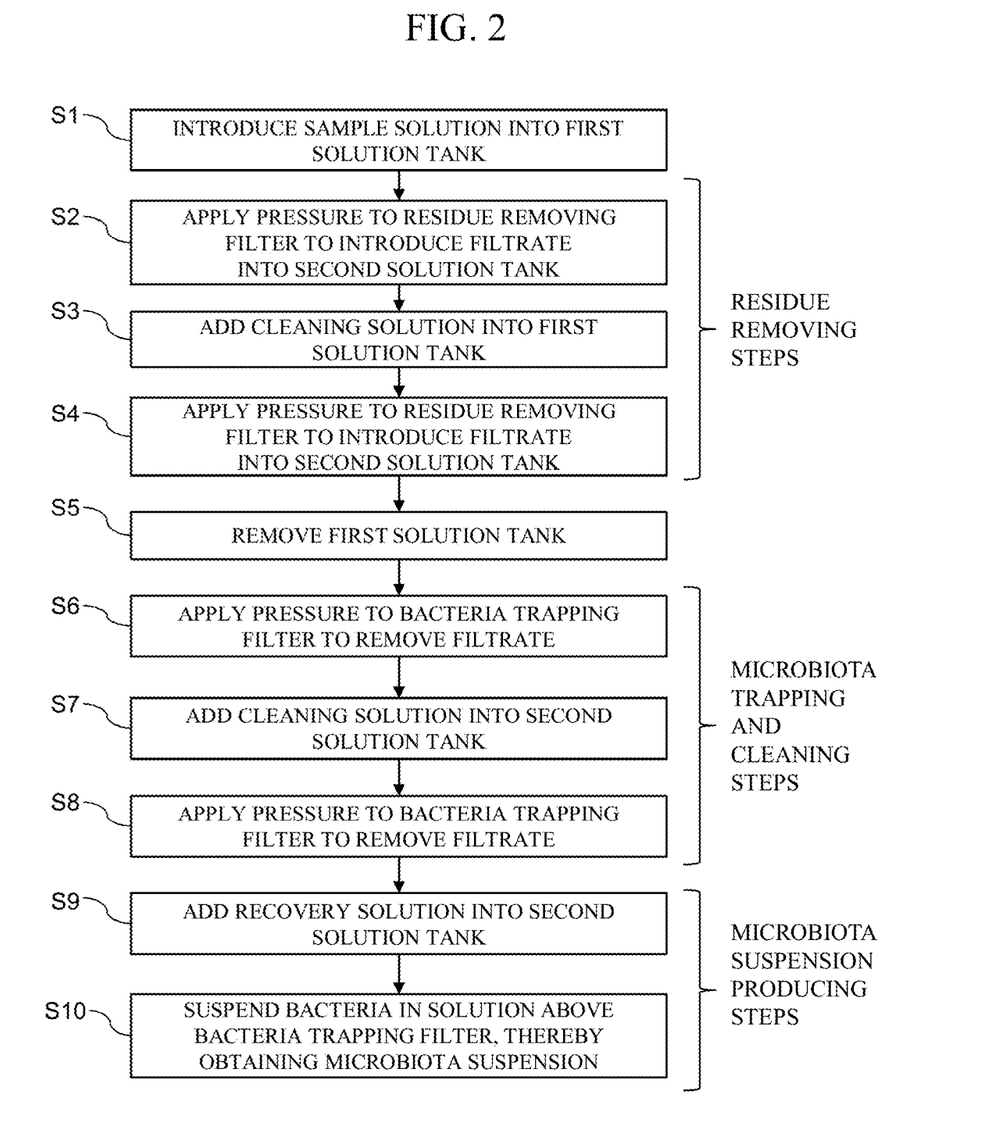
FIG. 2 is a flowchart illustrating a microbiota trapping method that uses the microbiota trapping apparatus according to the first embodiment.

FIG. 2 is a flowchart illustrating a microbiota trapping method that uses the microbiota trapping apparatus. Hereinafter, it is assumed that each of the aforementioned dispensing nozzles and the actuators is provided in or on the microbiota trapping apparatus, and the control device 100 controls the drive of each constituent element of the microbiota trapping apparatus so that the microbiota trapping operation is automatically performed.

In step S1, the control device 100 drives the sample container actuator to move the sample container, thereby introducing a sample solution into the first solution tank 101.

In step S2, the control device 100 drives the pressure container actuator to attach the pressure container 106 to the first solution tank 101. Then, the control device 100 drives the pressure pump 107 to generate a positive pressure so that the positive pressure (i.e., a first pressure) is applied to the residue removing filter 102 of the first solution tank 101. This allows the sample solution to be filtered through the residue removing filter 102 and allows the resulting filtrate to be introduced into the second solution tank 103, with residue having been removed. At this time, target bacteria to be trapped are introduced into the second solution tank 103 together with the filtrate.

As described above, since the gap 110 is provided between the first solution tank 101 and the second solution tank 103, the second solution tank 103 is maintained under the atmospheric pressure condition even when the first solution tank 101 is pressurized. That is, each of the first solution tank 101 and the second solution tank 103 can be pressurized independently. Thus, while the first solution tank 101 is pressurized to have residue removed from a sample solution, a solution that has been introduced into the second solution tank 103 is held therein without being filtered.

In step S3, the control device 100 drives the first dispensing nozzle actuator to cause the first dispensing nozzle to add a cleaning solution into the first solution tank 101. At this time, the cleaning solution may be added after the pressure container 106 is detached, or the pressure container 106 may be formed of a material that allows the first dispensing nozzle to penetrate therethrough.

In step S4, the control device 100 drives the pressure pump 107 to apply a pressure to the residue removing filter 102 of the first solution tank 101. This allows bacteria, which have stuck to an inner wall of the first solution tank 101 or to the residue removing filter 102, to be cleaned away and trapped into the second solution tank 103. Thus, the efficiency of recovering microbiota improves. It should be noted that each of steps S3 and S4 may be executed more than once or may not be performed at all. The number of times each of steps S3 and S4 is to be executed may be set to any value.

In the stage where the residue removing step is complete, the first solution tank 101 and the residue removing filter 102 become no more necessary. Thus, in step S5, the control device 100 drives the support 109 to evacuate the first solution tank 101 from above the second solution tank 103. This can prevent the first solution tank 101 from becoming a physical obstacle in the following steps. In addition, the control device 100 detaches the pressure container 106 from the first solution tank 101.

In step S6, the control device 100 drives the pressure container actuator to attach the pressure container 106 to the second solution tank 103. Then, the control device 100 drives the pressure pump 107 to apply a positive pressure (i.e., a second pressure) to the bacteria trapping filter 104 of the second solution tank 103. This allows the solution containing the bacteria to be filtered through the bacteria trapping filter 104 and thus allows the bacteria to be trapped by the bacteria trapping filter 104, and also allows the resulting filtrate to be introduced into the waste liquid container 105.

In step S7, the control device 100 drives the first dispensing nozzle actuator to cause the first dispensing nozzle to add a cleaning solution into the second solution tank 103.

In step S8, the control device 100 drives the pressure pump 107 to apply a pressure to the bacteria trapping filter 104 of the second solution tank 103. This allows substances other than the bacteria, which have stuck to the inner wall of the second solution tank 103 or to the bacteria trapping filter 104, to be cleaned away and discharged as a filtrate. Thus, the efficiency of recovering microbiota improves. It should be noted that each of steps S7 and S8 may be executed more than once or may not be performed at all. The number of times each of steps S7 and S8 is to be executed may be set to any value.

In step S9, the control device 100 drives the second dispensing nozzle actuator to cause the second dispensing nozzle to add a recovery solution into the second solution tank 103.

In step S10, the control device 100 drives the second dispensing nozzle actuator to cause the second dispensing nozzle to repeatedly suction and discharge the liquid in the second solution tank 103 within the second solution tank 103. Accordingly, a microbiota suspension is obtained in the second solution tank 103. Next, the control device 100 drives the second dispensing nozzle actuator to cause the second dispensing nozzle to dispense the microbiota suspension into a recovery container for recovering it.

Although an example has been described in which the control device 100 drives each constituent element of the microbiota trapping apparatus to automatically trap microbiota, the present application is not limited thereto. For example, a user may manually execute the aforementioned operations. In such a case, the user can attach or detach the pressure container 106, operate the pressure pump 107, move the first solution tank 101, and operate the first dispensing nozzle and the second dispensing nozzle, for example.

Technical Advantages

As described above, the microbiota trapping device 1 of the present embodiment can trap bacteria in a sample solution without performing centrifugation, and thus can reduce the burden on the user for operating the device. In addition, automating the operation for trapping microbiota using the microbiota trapping apparatus with the microbiota trapping device 1 can further reduce the burden on the user for operating the device.

There may be cases where the bacteria trapping filter 104 becomes clogged with microbiota while it is being trapped by the bacteria trapping filter 104 if the number of bacteria contained in the sample solution is large, which in turn can decrease the filtration speed. In such a case, if the first solution tank 101 and the second solution tank 103 are structured such that they are hermetically coupled together, a decrease in the filtration flow rate through the bacteria trapping filter 104 will cause a resistive pressure to act against the pressure applied to the residue removing filter 102, which in turn can disturb the filtration cleaning performed through the residue removing filter 102. In contrast, the microbiota trapping device 1 of the present embodiment has the gap 110 between the first solution tank 101 and the second solution tank 103. Thus, application of a pressure to the residue removing filter 102 and application of a pressure to the bacteria trapping filter 104 can be can performed independently, which can suppress a decrease in the filtration speed through the residue removing filter 102. Therefore, residue can be efficiently removed from the sample solution.

The gap 110 is also advantageous for changing the positional relationship between the first solution tank 101 and the second solution tank 103. If the first solution tank 101 and the second solution tank 103 are structured such that they are hermetically coupled together without the gap 110 provided therebetween, while the first solution tank 101 is pressurized, the second solution tank 103 would also be pressurized. Therefore, a greater force would be needed to evacuate the first solution tank 101 from the second solution tank 103. Further, if the first solution tank 101 and the second solution tank 103 are attempted to be separated from each other while they are pressurized, a sample would scatter upon release of the pressure. Then, the valuable sample may become lost due to the scattering or the scattered sample may contaminate the surrounding. In contrast, in the microbiota trapping device 1 of the present embodiment, the second solution tank 103 is maintained under the atmospheric pressure condition due to the presence of the gap 110. Thus, there is no possibility that a sample may scatter, which would otherwise occur upon release of a pressure when the first solution tank 101 is evacuated.

Second Embodiment

The aforementioned first embodiment illustrates an example in which the pressure container 106 is attached to the first solution tank 101 to pressurize it, and then, the pressure container 106 is attached to the second solution tank 103 to pressurize it so that residue is removed from a sample solution by the residue removing filter 102 and then microbiota is trapped by the bacteria trapping filter 104 as the sample solution is filtered therethrough. However, the pressurization method for the second solution tank 103 need not be the same as that for the first solution tank 101. For example, filtration through the bacteria trapping filter 104 may be implemented by applying a positive pressure to the first solution tank 101 and applying a negative pressure to the second solution tank 103.

Hereinafter, a second embodiment will describe an example in which the first solution tank 101 and the second solution tank 103 are provided with different pressurization mechanisms.

<Configuration of Microbiota Trapping Apparatus>

Figure 3:
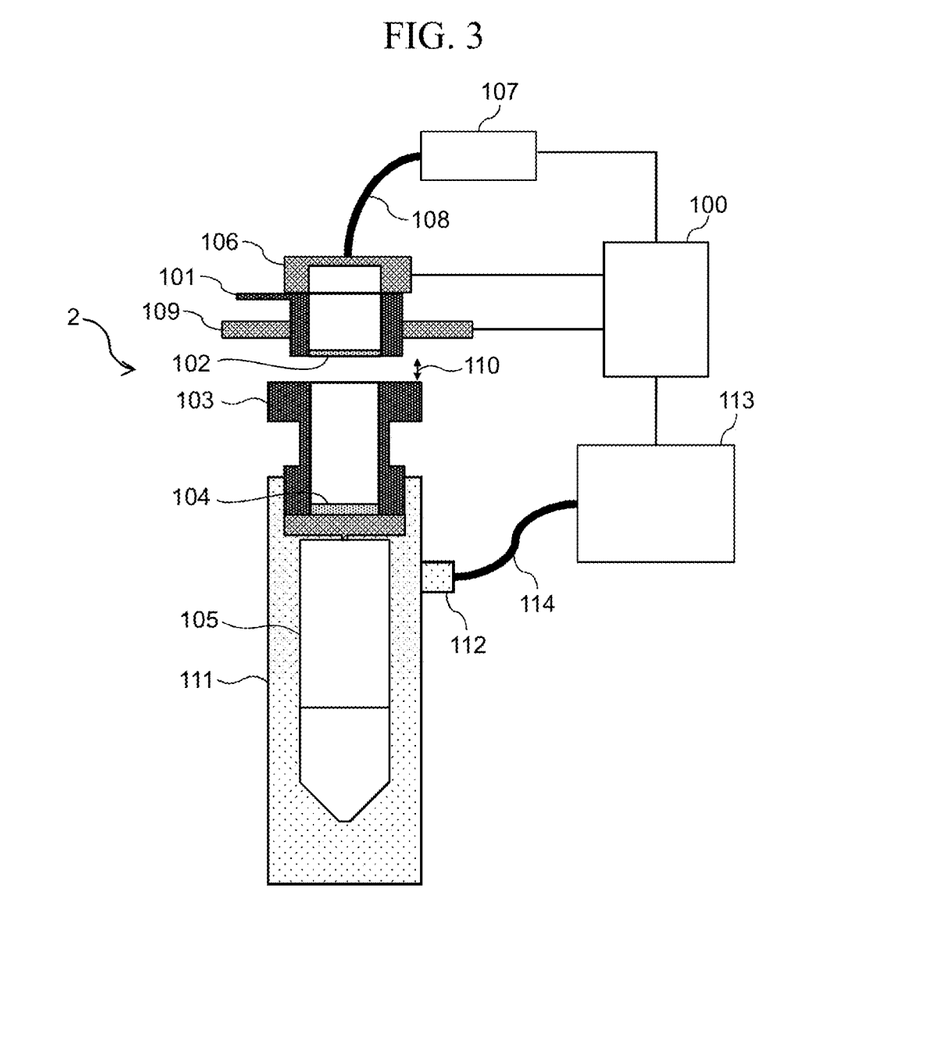
FIG. 3 is a schematic view of a microbiota trapping apparatus according to a second embodiment.

FIG. 3 is a schematic view of a microbiota trapping apparatus according to the second embodiment. As illustrated in FIG. 3, the microbiota trapping apparatus of the second embodiment differs from the microbiota trapping device 1 of the first embodiment in that a microbiota trapping device 2 includes a pressure container 111 (i.e., a pressure applicator) with an exhaust port 112, and the exhaust port 112 of the pressure container 111 and a depressurization pump 113 (i.e., a pressure applicator (or a negative pressure generator)) are coupled together by a tube 114.

The pressure container 111 covers the second solution tank 103 such that the bacteria trapping filter 104 and the waste liquid container 105 are located in the internal space of the pressure container 111. The exhaust port 112 and the depressurization pump 113 are coupled together by the tube 114, and the internal space of the pressure container 111 is hermetically sealed. A negative pressure generated by the depressurization pump 113 is applied to the pressure container 111. Examples of the pressure container 111 include a suction filtration container.

Instead of separately providing the pressure pump 107 (i.e., the positive pressure generator) and the depressurization pump 113 (i.e., the negative pressure generator), it is also possible to provide a single pressurization/depressurization pump having both the pressurization and depressurization functions and couple the pressure container 106 and the pressure container 111 to the pressurization/depressurization pump.

<Microbiota Trapping Method>

The microbiota trapping method of the present embodiment is substantially the same as that of the first embodiment illustrated in FIG. 2. Thus, only the differences will be described below.

In step S6, instead of switching the attachment target of the pressure container 106 to the second solution tank 103 to pressurize it, the depressurization pump 113 is driven to depressurize the pressure container 111 in the present embodiment. This allows a negative pressure (i.e., a second pressure) to be applied to the bacteria trapping filter 104 and thus allows a solution in the second solution tank 103 to be filtered by suction through the bacteria trapping filter 104, thereby trapping microbiota. In the present embodiment, step S5 illustrated in FIG. 2 may be performed after step S6.

Technical Advantages

As described above, the microbiota trapping apparatus of the present embodiment is configured such that a negative pressure is applied to the second solution tank 103 by the pressure container 111 and the depressurization pump 113 so that a solution containing bacteria is filtered by suction. This can eliminate the need to change the attachment target of the pressure container 106 and thus can execute the microbiota trapping operation more rapidly and easily in comparison with the first embodiment.

Third Embodiment

The aforementioned first embodiment and second embodiment each illustrate an example in which the gap 110 is provided between the bottom face (i.e., the residue removing filter 102) of the first solution tank 101 and the opening of the second solution tank 103. However, the position of the gap 110 is not limited thereto and can be changed as appropriate as long as each of the first solution tank 101 and the second solution tank 103 can be pressurized independently.

Hereinafter, a third embodiment will describe a microbiota trapping device with the position of the gap 110 changed.

<Configuration of Microbiota Trapping Device>

Figure 4A:
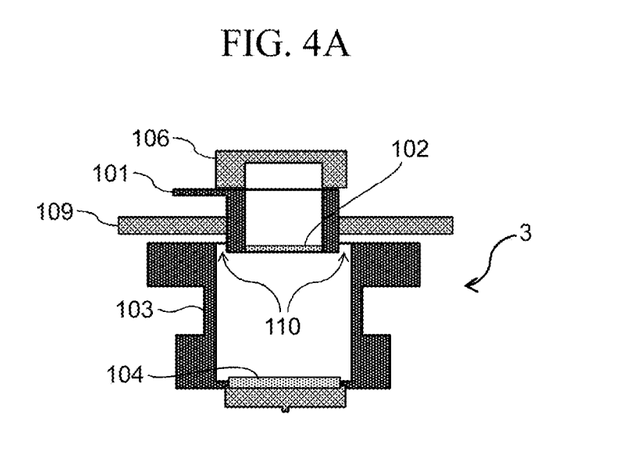
FIGS. 4A and 4B are schematic views of part of the configuration of a microbiota trapping device according to a third embodiment.

FIG. 4A is a schematic view of part of the configuration of a microbiota trapping device 3 according to the third embodiment. As illustrated in FIG. 4A, in the microbiota trapping device 3, the inside diameter of the second solution tank 103 is larger than the outside diameter of the first solution tank 101. The first solution tank 101 is supported by the support 109 such that the residue removing filter 102 is located within the second solution tank 103 and the outer wall of first solution tank 101 is not in contact with the inner wall of the second solution tank 103. Accordingly, the gap 110 is formed between the side of the residue removing filter 102 of the first solution tank 101 and the inner wall of the second solution tank 103.

Figure 4B:
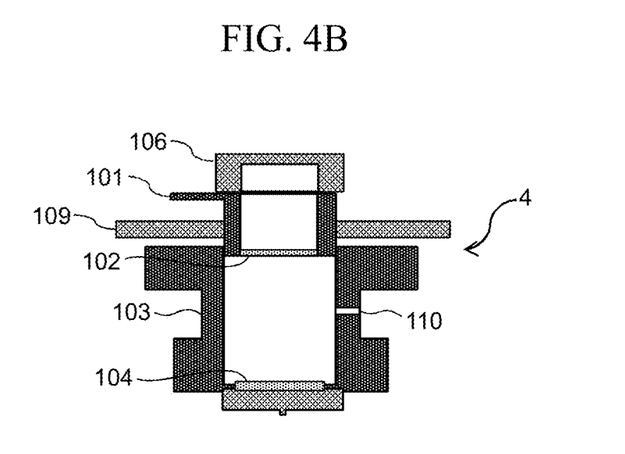

FIG. 4B is a schematic view of part of the configuration of a microbiota trapping device 4. As illustrated in FIG. 4B, the gap 110 may be formed in the form of a through-hole in the side wall of the second solution tank 103. The through-hole (i.e., a vent) is provided above the bacteria trapping filter 104, and thus can maintain the interior of the second solution tank 103 at an atmospheric pressure when the second solution tank 103 is not pressurized. In FIG. 4B, the outside diameter of the first solution tank 101 is set substantially equal to the inside diameter of the second solution tank 103 so that an end of the first solution tank 101 can be fitted into the opening of the second solution tank 103.

With the adoption of the configuration in FIG. 4B, it becomes less likely for external matter to intrude into the second solution tank 103, which can reduce the risk of contamination.

In the microbiota trapping device 3 of FIG. 4A and the microbiota trapping device 4 of FIG. 4B, either the pressurization mechanism of the first embodiment or that of the second embodiment can be adopted for each of the first solution tank 101 and the second solution tank 103.

<Microbiota Trapping Method>

In the present embodiment, the same microbiota trapping method of the first embodiment or the second embodiment can be adopted. Thus, the description thereof is omitted herein.

Technical Advantages

As described above, the space of the gap 110 in each of the microbiota trapping devices 3 and 4 of the present embodiment can be reduced than those of the first embodiment and the second embodiment. Accordingly, contamination of the second solution tank 103 from the outside can be suppressed.

EXAMPLES

Hereinafter, Examples of the present disclosure will be described.

Example 1

<Preparation of Samples>

Four types of pure-cultured bacterial cells, including *Escherichia coli*, *Pseudomonas aeruginosa*, *Staphylococcus aureus*, and *Enterococcus faecalis*, were obtained by performing overnight shaking culture using an LB culture medium.

The optical density of each bacterial body solution was measured and was adjusted to attain O.D.=1. The number of bacterial cells, which has a value of $1\times10^8$ CFU, in 1 mL of a bacterial body solution with O.D.=1 was used as the index, and equal amounts of the four types of bacterial body solutions were mixed to produce a mixed bacterial body solution with a total bacterial count of $1\times10^9$ CFU or $1\times10^{10}$ CFU as model microbiota.

2.5 g of "Ukigoi" as floating carp (manufactured by MARUKYU CO., LTD.), which is fishing bait, 1 g of "Kameliya (registered trademark)" hard wheat flour (manufactured by Nisshin Seifun Group Inc.), and 2.5 g of sterile water were mixed in the thus produced model microbiota so as to produce a simulated fecal model sample. Then, the simulated fecal model sample was stored at −20° C. for use in the following steps.

<Preparation of Microbiota Trapping Device>

In Example 1, a microbiota trapping apparatus was constructed by preparing six microbiota trapping devices 2 of the second embodiment illustrated in FIG. 3 and coupling them to their respective control devices 100. As the constituent elements of the microbiota trapping apparatus, the following were specifically used.

The first solution tank 101 and the residue removing filter 102: A Falcon (registered trademark) cell strainer (having a mesh with a pore size of 100 μm) manufactured by Corning Incorporated was used.

The second solution tank 103: A holder for holding the bacteria trapping filter 104 was produced with a 3D printer and used as the second solution tank 103.

The bacteria trapping filter 104: A Millipore Express (registered trademark) PLUS membrane filter (with a pore size of 0.45 μm) manufactured by Merck KGaA was used.

The waste liquid container 105: A Falcon (registered trademark) 50 mL conical tube manufactured by Corning Incorporated was used.

The pressure container 106: An aluminum pressure container was produced and used as the pressure container 106.

The pressure container 111: A suction-filtration container was used.

The pressure pump 107 and the depressurization pump 113: A diaphragm vacuum pump N86KN.18 (i.e., a pressurization/depressurization pump) manufactured by KNF Group was used.

The tubes 108 and 114: Silicone tubes were used.

<Method of Removing Residue from Sample>

A process of removing residue from the fecal model sample was performed with the following procedures. The following steps and tests were conducted with the six microbiota trapping devices 2 (test Nos. 1 to 6) using the same sample under the same conditions.

Step 1: The fecal model sample was dissolved in 2 mL of a PBS solution so that the sample was suspended in the solution and a sample solution was thus obtained.

Step 2: The membrane filter (i.e., the bacteria trapping filter) was put on the second solution tank and the waste liquid container was coupled to the bottom of the second solution tank. In addition, the cell strainer (i.e., the first solution tank and the residue removing filter) was disposed above the second solution tank. The gap between the second solution tank and the cell strainer was set to about 1 mm. Then, the sample solution was added into the cell strainer.

Step 3: The pressurization/depressurization pump was set to a pressurization condition so as to pressurize the cell strainer for 1 minute so that the sample solution was filtered and the resulting filtrate was introduced into the second solution tank.

Step 4: 1 mL of a PBS solution was added into the cell strainer.

Step 5: The cell strainer was pressurized for 1 minute as in step 3 to effect filtration, and the resulting filtrate was introduced into the second solution tank.

Step 6: The cell strainer was removed from above the second solution tank.

<Trapping of Bacterial Cells>

Trapping of bacterial cells and cleaning of the membrane filter were performed with the following procedures.

Step 7: The second solution tank and the waste liquid container were disposed in the suction-filtration container, and the exhaust port of the suction-filtration container and the pressurization/depressurization pump were coupled together with the silicone tube. Next, suction was performed by the pressurization/depressurization pump so that the degree of vacuum in the suction-filtration container was increased (i.e., the suction-filtration container was depressurized) and thus a negative pressure was applied to the membrane filter (i.e., the bacteria trapping filter) and the filtrate was separated.

Step 8: 3 mL of a PBS solution was added into the second solution tank.

Step 9: 3 mL of a PBS solution was added into the second solution tank.

Step 10: 2 mL of a TE solution was added into the second solution tank.

Step 11: 2 mL of a TE solution was added into the second solution tank.

Step 12: 2 mL of a TE solution was added into the second solution tank.

Step 13: Depressurization was stopped after the filtrate had been separated.

It should be noted that Steps 8 to 12 were performed while depressurization by the pressurization/depressurization pump was continued.

Herein, it was observed that the pressurization time differs depending on bacteria and suspended matter contained in the sample used. If the sample used is a clean sample close to pure water, it will take several ten seconds to filter 3 mL of the solution, for example. Meanwhile, if the sample used contains a large amount of suspended matter, such as feces, it may take about 2 hours to filter 3 mL of the solution. Therefore, the time (i.e., depressurization time) for performing a filtration process can be appropriately adjusted according to the state and amount of the sample added. In addition, for the purpose of cleaning the membrane filter and the second solution tank, a cleaning solution is added into the second solution tank in the next step after the solution added into the second solution tank has sufficiently passed therethrough. Specifically, cleaning is continued until the amount of the solution remaining on the membrane filter becomes less than 200 µL per cleaning. The number of times cleaning is to be performed as well as the amount of the solution to remain on the membrane filter can be appropriately set by the user.

<Recovery of Bacterial Body Suspension>

Bacterial cells were recovered with the following procedures.

Step 14: 800 µL of a TE solution was added into the second solution tank.

Step 15: A micropipette was used with its volume set to 600 µL, and the bacterial cells and the TE solution were pipetted up and down 10 times within the second solution tank. Accordingly, a bacterial body suspension was obtained.

Step 16: the bacterial body suspension was recovered into the recovery container.

<DNA extraction test>

Genomic DNA was extracted from the thus obtained bacterial body suspension according to the method described in Non Patent Literature 2 (i.e., the method using enzymes), and was then electrophoresed on 0.8% of an agarose gel.

Figure 5:
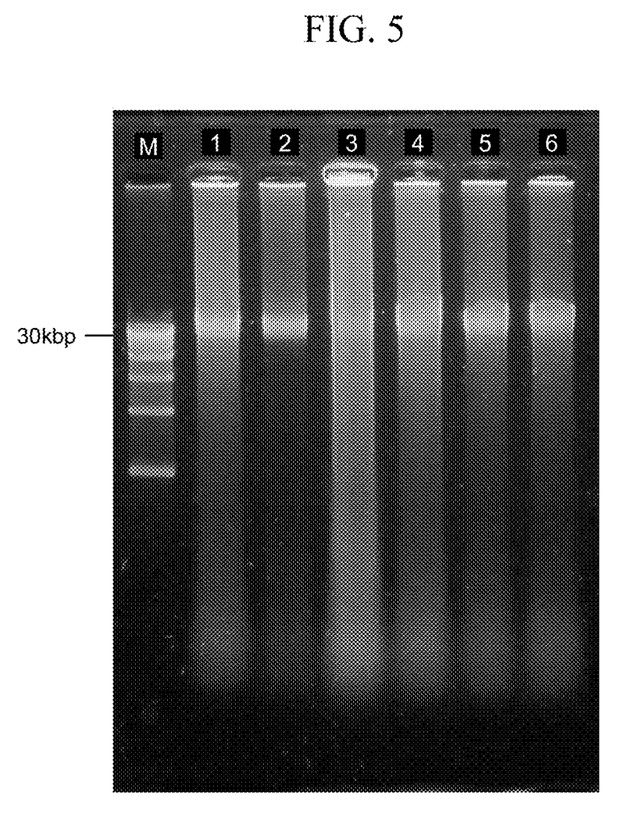
FIG. 5 is a view illustrating the results of electrophoresis of DNA that has been extracted from microbiota in an extraction test of Example 1.

FIG. 5 illustrates the results of electrophoresis of DNA extracted from the microbiota. A lane M is a size marker serving as the index of the base length. Lanes 1 to 6 correspond to test Nos. 1 to 6, respectively.

As illustrated in FIG. 5, it is found that long-chain DNA with a size of over 30 kbp was able to be extracted in each test.

<Measurement of Proportions of Bacterial Species in Bacterial Body Suspension>

Microbiota-derived DNA extracted in the aforementioned extraction test was subjected to quantitative PCR using QuantStudio (registered trademark) manufactured by Thermo Fisher Scientific K.K. so that the proportions of bacterial species contained in the DNA solution were calculated.

As a reference example, the steps of removing residue up to recovering microbiota were performed on the fecal model sample produced in Example 1 according to the method described in Non Patent Literature 2 instead of using the microbiota trapping device. Then, quantitative PCR was performed thereon using QuantStudio (registered trademark) manufactured by Thermo Fisher Scientific K.K.

Figure 6A:
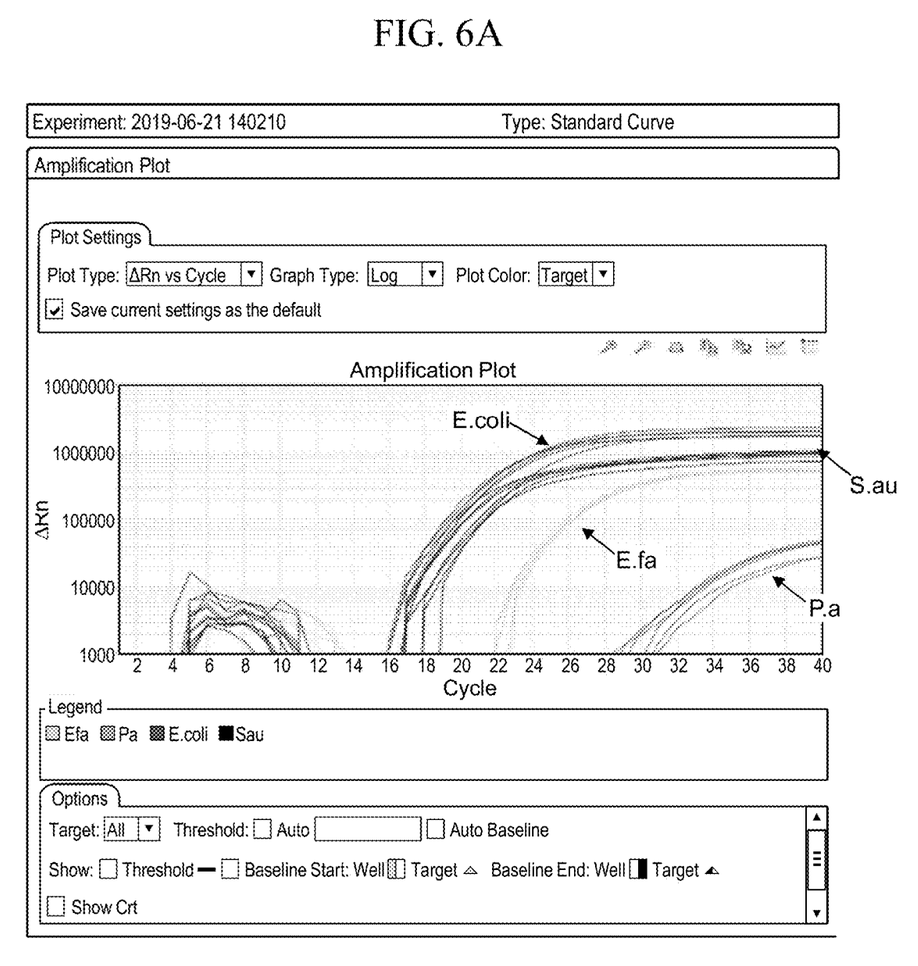
FIGS. 6A and 6B are graphs each illustrating the results of quantitative PCR performed on microbiota-derived DNA.
Figure 6B:
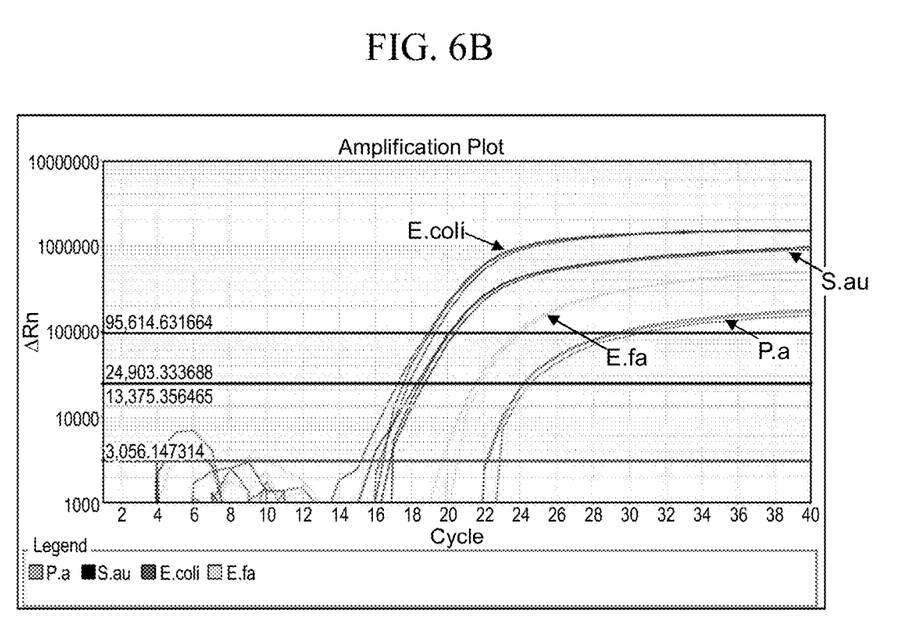

FIGS. 6A and 6B illustrate the results of quantitative PCR performed on the microbiota-derived DNA. FIG. 6A illustrates the results of recovering microbiota using the microbiota trapping device of Example 1 and extracting DNA from the microbiota, and then performing quantitative PCR thereon. FIG. 6B illustrates the results of recovering microbiota according to the method described in Non Patent Literature 2 and extracting DNA from the microbiota, and then performing quantitative PCR thereon. In each of FIGS. 6A and 6B, the results of the six tests (test Nos. 1 to 6) are illustrated in one graph.

As illustrated in FIG. 6A, it is confirmed that according to Example 1, microbiota was able to be recovered irrespective of the bacterial species included therein. In addition, comparing FIGS. 6A and 6B can confirm that the result of the quantitative PCR of Example 1 is quite similar to that of the reference example. Thus, it is recognized that using the microbiota trapping device of Example 1 can recover microbiota to about the same extent as that of the conventional method of trapping microbiota that includes removing residue through a filter and performing centrifugation.

[Variation]

The present disclosure is not limited to the aforementioned embodiments and includes a variety of variations. For example, although the aforementioned embodiments have been described in detail to clearly illustrate the present disclosure, the present disclosure need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

DESCRIPTION OF SYMBOLS

1 to 3 Microbiota trapping device
100 Controller
101 First solution tank
102 Residue removing filter
103 Second solution tank
104 Bacteria trapping filter
105 Waste liquid container
106 Pressure container
107 Pressure pump
108 Tube
109 Support
110 Gap
111 Pressure container
112 Exhaust port
113 Depressurization pump
114 Tube

What is claimed is:

1. A microbiota trapping method using a microbiota trapping device, the microbiota trapping device including a first solution tank having a first filter adapted to trap residue in a sample, a second solution tank having a second filter adapted to trap bacteria in the sample, and a support that supports the first solution tank above the second solution tank, the support being adapted to support the first solution tank so that a gap is formed between the first solution tank and the second solution tank and allowing an opening of the second solution tank to serve as a vent, the microbiota trapping method comprising:
   introducing the sample into the first solution tank;
   applying a first pressure to only the first solution tank, thereby causing the first filter to trap the residue in the sample and introducing a filtrate containing the bacteria into the second solution tank; and
   applying a second pressure to only the second solution tank, thereby causing the second filter to trap the bacteria in the filtrate.

2. The microbiota trapping method according to claim 1, wherein a first pore size of the first filter is greater than or equal to 70 µm, and a second pore size of the second filter is less than or equal to 1 µm.

3. The microbiota trapping method according to claim 1, wherein each of the first pressure and the second pressure is a positive pressure.

4. The microbiota trapping method according to claim 1, wherein the first pressure is a positive pressure and the second pressure is a negative pressure.

5. The microbiota trapping method according to claim 1, further comprising adding a recovery solution into the second solution tank to suspend the bacteria in the recovery solution, thereby obtaining a microbiota suspension.

* * * * *